(12) United States Patent
Takaki et al.

(10) Patent No.: US 6,623,664 B2
(45) Date of Patent: Sep. 23, 2003

(54) CONDUCTIVE ADHESIVE AND BIOMEDICAL ELECTRODE

(75) Inventors: Shunsuke Takaki, Sagamihara (JP); Toshihiro Suwa, Sagamihara (JP)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 10/130,591

(22) PCT Filed: Dec. 21, 2000

(86) PCT No.: PCT/US00/35063

§ 371 (c)(1), (2), (4) Date: May 16, 2002

(87) PCT Pub. No.: WO01/48111

PCT Pub. Date: Jul. 5, 2001

(65) Prior Publication Data

US 2003/0088239 A1 May 8, 2003

(30) Foreign Application Priority Data

Dec. 24, 1999 (JP) ............................................. 11-367619

(51) Int. Cl.$^7$ ............................. H01B 1/12; C09J 9/02; A61L 24/00; A61B 5/0408; A61N 1/04
(52) U.S. Cl. ...................... 252/511; 252/500; 252/510; 156/327; 424/448
(58) Field of Search ................................. 252/500, 510, 252/511; 156/327, 328; 424/448

(56) References Cited

U.S. PATENT DOCUMENTS

| 4,289,844 A | 9/1981 | Specht et al. |
| 4,406,827 A | 9/1983 | Carim |
| 4,524,087 A | 6/1985 | Engel |
| 4,539,996 A | 9/1985 | Engel |
| 4,554,924 A | 11/1985 | Engel |
| 4,588,762 A | 5/1986 | Mruk et al. |
| 4,715,382 A | 12/1987 | Strand |
| 4,771,713 A | 9/1988 | Kinzenbaw |
| 4,846,185 A | 7/1989 | Carim |
| 4,848,353 A | 7/1989 | Engel |
| 5,012,810 A | 5/1991 | Strand et al. |
| 5,078,139 A | 1/1992 | Strand et al. |
| 5,133,356 A | 7/1992 | Bryan et al. |
| 5,270,358 A | 12/1993 | Asmus |
| 5,338,490 A | * 8/1994 | Dietz et al. .................. 252/500 |
| 5,512,272 A | * 4/1996 | Krzysik ....................... 424/59 |
| 5,670,557 A | 9/1997 | Dietz et al. |
| 5,779,632 A | 7/1998 | Dietz et al. |
| 2001/0018568 A1 | * 8/2001 | Iga et al. ....................... 424/59 |

FOREIGN PATENT DOCUMENTS

| JP | 2570183 Y | 1/1993 |
| JP | 8-193494 | 7/1996 |
| WO | WO 97/41568 | 11/1997 |
| WO | WO 00/09203 | 2/2000 |

* cited by examiner

Primary Examiner—Mark Kopec
Assistant Examiner—Kallambella Vijayakumar
(74) Attorney, Agent, or Firm—Daniel R. Pastirik

(57) ABSTRACT

The conductive adhesive of the present invention has a multi-layer structure comprising a hydrophobic phase containing an adhesive polymer, and a hydrophilic phase containing an electrolyte. This conductive adhesive is superior in anti-drying effect (moisturizing effect) because a humectant is effectively contained in the hydrophilic phase. The present invention also relates to a biomedical electrode using such a conductive adhesive. In the biomedical electrode according to the present invention, an adhesive layer to be applied to the skin surface of the human body contains the conductive adhesive described above and an electrode terminal connected with the adhesive layer is provided.

6 Claims, 1 Drawing Sheet

US 6,623,664 B2

CONDUCTIVE ADHESIVE AND BIOMEDICAL ELECTRODE

FIELD OF THE INVENTION

The present invention relates a conductive adhesive which develops conductivity through the medium of an electrolyte contained therein and, more particularly, to a conductive adhesive suited for use as a biomedical electrode.

BACKGROUND OF THE INVENTION

A biomedical electrode is usually composed of a conductive layer to be made in contact with the skin of mammals (including human) and an electrode connected electrically with the conductive layer, and is used in various applications depending on its construction. For example, a biomedical electrode can be used for electrical diagnosis, treatment or surgery of mammals. As a device for measuring a cardiac action potential, for example, the biomedical electrode is applied to the surface of the living body. In such a case, the biomedical electrode detects a change in potential on the surface of the living body in an electrocardiograph for measuring and recording a cardiac action potential. A change in potential on the surface of the living body, detected by such a biomedical electrode, is inputted into an electrocardiograph equipped with the biomedical electrode, recorded as an information of an electrocardiogram, and then displayed or printed. A terminal of the biomedical electrode is connected to the electrocardiograph through a connection cable or lead wire.

The above-described biomedical electrodes can comprise, for example, an Ag/AgCl conductor eyelet, a stud of carbon (or metal) as an electrode terminal, and a conductive non-adhesive gel layer as a conductive layer to be placed in contact with the skin surface. Such a conductive non-adhesive gel is disclosed, for example, in Japanese National Publication (Kohyo) No. 56501108; or corresponding U.S. Pat. No. 4,406,827 and Japanese Utility Model Registration No. 2570183. It is necessary that such a biomedical electrode further comprises an adhesive tape (backing tape) for fixing it to the surface of the living body. Biomedical electrodes that include a conductive adhesive layer as a conductive layer, however, do not require the adhesive tape.

A conductive adhesive, which can be used as the above-described conductive adhesive layer, is disclosed in Japanese Examined Patent Publication (Kokoku) No. 8-19394 and U.S. Pat. No. 4,524,087. A biomedical electrode utilizing a conductive adhesive is disclosed in U.S. Pat. No. 5,078,139. Such biomedical electrodes can be fixed to the surface of the living body without containing a backing adhesive tape for fixing, and can comprise:

(a) a conductive adhesive layer containing an aqueous electrolyte solution and an adhesive polymer, (b) a liner for coating one surface (adhesive surface) of the conductive adhesive layer, (c) a backing for coating the other surface of the conductive adhesive layer, and (d) an electrode terminal connected with the conductive adhesive layer, which has an exposed portion coated neither with the liner nor backing.

When this biomedical electrode is applied to the skin, the electrode can be readily fixed only by peeling off the liner to expose one surface of the conductive adhesive layer, and bringing the adhesive surface into contact with the surface of the living body thereby to slightly contact-bond them. A conventional conductive adhesive layer has sufficient initial adhesive strength, but as a result of absorption of sweat from the skin into the adhesive layer the adhesive strength is likely lowered over time.

U.S. Pat. Nos. 5,779,632 and 5,670,557 disclose a so-called "bicontinuous conductive adhesive" having a continuous structure comprising a hydrophilic conductive phase containing an aqueous electrolyte solution and a hydrophobic adhesive phase. In such a bicontinuous conductive adhesive, the hydrophilic phase containing an electrolyte is a continuous layer and ionic conductivity can be exhibited. Since the hydrophobic adhesive layer has a bonding function and sweat from the skin is absorbed by the hydrophilic phase, lowering of the adhesion strength can be improved. In the bicontinuous conductive adhesive (or biomedical electrode using the same), however, it was particularly difficult to retain water content during storage under low humidity conditions. Accordingly, the biomedical electrode must be stored in a sealed pouch to prevent drying (vaporization) of the phase including the aqueous electrolyte. It is also normally necessary to use the biomedical electrode within 10 to 30 days after opening the sealed pouch since, it becomes difficult to obtain sufficient electrical characteristics (i.e., sufficiently low impedance) when the conductive adhesive dries.

U.S. Pat. No. 5,338,490 discloses an adhesive comprising (A) a first phase containing a hydrophilic polymer and an aqueous solution of electrolyte, and (B) a second phase containing a hydrophobic adhesive polymer, wherein the first phase is a continuous phase and the second phase is a domain phase contained in the state of being dispersed in the first phase.

U.S. Pat. No. 5,270,358 discloses a so-called "bidispersed" adhesive composition comprising a continuous phase of a hydrophobic pressure-sensitive adhesive and a hydrophilic dispersed phase of a hydrogel having pressure-sensitive adhesion characteristics. However, this adhesive composition has no ionic conductivity because the hydrophilic dispersed phase (each particle of hydrogen) is not a continuous phase and, therefore, the adhesive composition can not be used as the conductive adhesive.

It is desirable to include a humectant in the conductive adhesive of a biomedical electode to impede drying of the conductive adhesive. However, when high-performance humectants such as amino acids are added to the bicontinuous conductive adhesive to obtain a high moisturizing effect, an expected two-phase structure can not be obtained. That is, when a comparatively large amount of the humectant exists, a continuous structure of a hydrophobic adhesive phase is likely broken into an emulsion as a raw material of the conductive adhesive, thereby making it difficult to maintain the structure in an effective state (e.g. a state where sufficient adhesion property can be exhibited).

SUMMARY OF THE INVENTION

In one aspect the present invention provides a conductive adhesive comprising:

(A) a first phase containing a hydrophilic polymer, an aqueous electrolyte solution and a humectant, and (B) a second phase containing a hydrophobic adhesive polymer, characterized in that:

the first phase is a continuous phase and the second phase is a domain phase that is dispersed in the first phase, and the domain phase has an average diameter within a range from 0.02 $\mu$m to 1 mm.

In another aspect, the present invention provides a biomedical electrode comprising an adhesive layer containing the conductive adhesive of the present invention, and an electrode terminal connected with the adhesive layer.

DETAILED DESCRIPTION OF PREFERRED EMBODIMENTS

Figure 1:
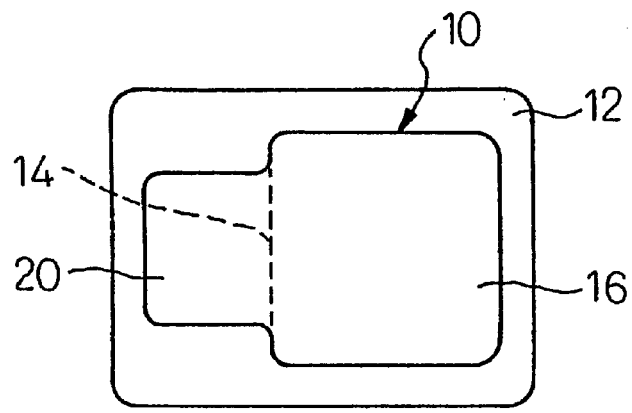
FIG. 1 is a planar view showing one preferred embodiment of a biomedical electrode according to the present invention.

The conductive adhesive and biomedical electrode according to the present invention can be advantageously carried out in various aspects as described in detail below.

The conductive adhesives of the present invention is characterized, in their essential aspects, by a conductive adhesive that comprises: (A) a first phase containing a hydrophilic polymer, an aqueous electrolyte solution and a humectant (collectively referred to as the "hydrophilic phase" unless otherwise stated because it usually is hydrophilic) and (B) a second phase containing a hydrophobic adhesive polymer (referred to as a "hydrophobic phase" unless otherwise stated because it usually is hydrophobic), wherein the hydrophilic phase is a continuous phase and the hydrophobic phase is a domain phase dispersed in the first phase. In such a dispersed adhesive having a two-phase structure, since the hydrophobic phase is originally a domain phase, it is easy to maintain a stable phase structure in a comparatively wide composition range and prevent breakage of the phase structure. Accordingly, a humectant can be effectively added to the continuous phase (i.e. the hydrophilic phase) to enhance the moisturizing effect and effectively prevent drying of the conductive adhesive (or conductive adhesive layer of the biomedical electrode). That is, according to the present invention, a humectant having a high moisturizing effect can be used.

In this dispersed adhesive having a two-phase structure, since the hydrophilic phase containing an electrolyte is a continuous phase, the ionic conductivity is high and the adhesive is suitably used as the conductive adhesive.

An average diameter of the domain phase constituting the adhesive can be appropriately decided depending on desired performance characteristics such as humidity retention effect and the like. Average diameters within a range from about 0.02 $\mu$m to about 1 mm can be used. When the average diameter of the domain phase is smaller than about 0.02 $\mu$m, the composition range capable of maintaining the phase structure may become narrow. Narrow composition ranges make it difficult to mix a requisite amount of high-performance humectant (e.g. amino acids, etc.), thereby limiting the moisturizing effect. In other words, to incorporate a requisite amount of high-performance humectants (e.g. amino acids, etc.) to enable easy and stable retention of the phase structure, it is suitable to increase the average diameter of the domain phase to the predetermined lower limit or more. On the other hand, when the average diameter exceeds 1 mm, it becomes difficult to form and maintain the domain phase and it is likely to become difficult to produce an adhesive having a uniform structure. When the structure of the adhesive becomes uniform, it becomes difficult to control the adhesion property and conductivity within a desired range. Accordingly, the average diameter of the domain phase is preferably within a range from about 0.03 to about 100 $\mu$m, and more preferably from about 0.04 to about 10 $\mu$m.

Any known humectant composition may be used in the present invention. Generally, preferred humectants will be compatible with and soluble in the hydrophilic phase of the conductive adhesive. Amino acids are a preferred class of humectant compounds.

The adhesive is preferably prepared in the following manner to enhance a moisturizing effect.

First step:
  A stock solution is prepared that comprises:
  (a) an aqueous medium containing a first monomer capable of forming a hydrophilic polymer after polymerization and a humectant composition, and
  (b) a second monomer capable of forming a hydrophobic adhesive polymer after polymerization, which is dispersed in the aqueous medium.

Second step:
  The stock solution prepared in the first step is subjected to a polymerization treatment, to obtain a precursor syrup solution (as an adhesive precursor) that comprises:
  (1) a continuous phase formed from the aqueous medium, and
  (2) a domain phase, which is dispersed in the continuous phase of the aqueous medium and contains the hydrophobic adhesive polymer.

Third step:
  The precursor syrup solution obtained in the second step can be further subjected to a polymerization treatment to form a conductive adhesive of the present invention.

Using the above preparation method, since a continuous and hydrophilic phase and a hydrophobic adhesive domain phase are formed upon polymerization of each starting monomers, it becomes easy to chemically bond the phases and effectively increase the stability of the resulting phase structure. Accordingly, it becomes possible to effectively utilize a humectant, (particularly an amino acid humectant) and thus effectively prevent undesired drying.

In the first step of the above-described preparation method, a dispersed phase containing a second monomer is usually dispersed in a continuous phase containing an aqueous medium by a mixing/dispersion operation such as stirring. In the second step, all or portion of the second monomer is polymerized to form a domain phase containing a hydrophobic adhesive polymer. The dispersion stability of the domain phase containing the hydrophobic adhesive polymer thus prepared is very high, thereby making it possible to effectively prevent the dispersed structure from breaking by the presence of the humectant. When the dispersed structure of the domain phase is broken the adhesion property and conductivity are lowered.

It is easy to impart a comparatively low viscosity, which is advantageous to conduct a coating or immersing operation, to the adhesive precursor syrup prepared in the second step. Accordingly, it is very easy to further subject the precursor syrup solution formed as a layer by coating to a polymerization treatment in the third step, thereby forming a conductive adhesive layer. Accordingly, the adhesive is particularly suited to form a conductive adhesive layer used as a biomedical electrode.

Another aspect of the present invention provides a biomedical electrode comprising an adhesive layer containing a conductive adhesive, and an electrode terminal connected with the adhesive layer. According to this biomedical electrode, the anti-drying effect (moisturizing effect) of the adhesive layer can be effectively enhanced without lowering the adhesion property and conductivity. Such a biomedical electrode can be maintained for a long period of time without being dried even when allowed to stand under a low-humidity condition outside a sealed pouch. The conductive adhesive of the present invention can also be used as a composition for uses other than as an adhesive layer.

The conductive adhesive of the present invention, components constituting the conductive adhesive, methods of preparing the adhesive using those components, biomedical electrodes and methods of producing the same are now described below. It will be appreciated that the conductive adhesive and biomedical electrode of the present invention are not limited by the following descriptions.

Conductive Adhesive

As described above, in the conductive adhesive of the present invention, a domain phase dispersed in a hydrophilic continuous phase (hydrophilic phase) comprises a hydrophobic adhesive polymer. Such a hydrophobic phase exists as a domain phase dispersed stably in a continuous phase of a hydrophilic phase.

The above stable domain phase can be formed in the following procedure.

First, a stock solution is prepared that comprises:
(a) an aqueous medium containing a first monomer capable of forming a hydrophilic polymer after polymerization and a humectant,
(b) a second monomer capable of forming a hydrophobic adhesive polymer after polymerization, which is dispersed in the aqueous medium, and
(c) an oil-soluble polymerization initiator.

The solution is then subjected to a polymerization treatment to form a precursor syrup solution comprising a continuous phase formed from the aqueous medium and a domain phase, which is dispersed in the continuous phase and contains the hydrophobic adhesive polymer.

The above stock solution used for formation of the precursor syrup solution as the adhesive precursor is usually prepared by dispersing a dispersed phase containing the second monomer and oil-soluble polymerization initiator in the continuous phase containing the aqueous medium by a mixing/dispersion operation such as stirring. In this way, a comparatively stable dispersed phase can be formed with an appropriate surfactant contained in the stock solution or by utilizing appropriate stirring conditions.

In the case where the precursor syrup solution is subjected to a polymerization operation to obtain a conductive adhesive as final product, it is comparatively difficult to form a domain phase containing a hydrophobic adhesive polymer having a predetermined size. Therefore, the stock solution subjected to this dispersion operation is preferably subjected to a polymerization treatment (first polymerization treatment) to polymerize all or portion of the second monomer, thereby stabilizing the domain phase containing the hydrophobic adhesive polymer. The dispersion stability of the domain phase thus formed is very high, thereby making it possible to effectively prevent the dispersed structure from breaking by the presence of the humectant. Then, a water-soluble polymerization initiator is added to the precursor syrup solution formed as described above and is further subjected to a polymerization treatment (second polymerization treatment) to form a conductive adhesive of the present invention. In this stage, substantially all of the above first and second monomers are polymerized. The hydrophilic polymer formed from the first monomer constitutes a hydrophilic phase as a continuous phase in the finally-obtained conductive adhesive. According to such a method, the conductive adhesive as the final product can be obtained while the domain phase containing the hydrophobic adhesive polymer formed in the precursor syrup solution is stably maintained.

Since the domain phase contained in the precursor syrup solution is very stable, a coating solution having the viscosity suited for coating can also be formed by adding a diluting solvent such as water to the precursor syrup solution. To crosslink the hydrophilic polymer and/or hydrophobic polymer, a crosslinking agent can also be added to the precursor syrup solution before the final polymerization operation.

As described above, one embodiment of the present invention also provides a preferred precursor syrup solution so as to form a conductive adhesive. That is, there is provided a precursor syrup solution formed by subjecting a stock solution comprising:
(a) an aqueous medium containing a first monomer capable of forming a hydrophilic polymer after polymerization, and a humectant,
(b) a second monomer capable of forming a hydrophobic adhesive polymer after polymerization, which is dispersed in the aqueous medium, and
(c) an oil-soluble polymerization initiator.

Non-indented to a polymerization treatment, said precursor syrup solution comprising:
a continuous phase formed from the aqueous medium, and
a domain phase which is dispersed in the continuous phase and contains the hydrophobic adhesive polymer. The precursor syrup solution is used for forming a conductive adhesive by further subjecting to a polymerization treatment.

Method of Producing Conductive Adhesive

In accordance with its preferred aspect, the adhesive of the present invention is composed of a domain phase of a hydrophobic adhesive polymer, and a hydrophilic and ionic conductive continuous phase, and has a white or opaque emulsion structure. The average diameter of the domain phase (hydrophobic phase) is within a range from about 0.02 $\mu$m to about 1 mm. Such an emulsion is usually referred to as a macro- or micro-emulsion.

The structure of the macro- or micro-emulsion can be preferably formed in the following procedure. First, a precursor syrup solution (as an adhesive precursor) of an emulsion stabilized by UV irradiation or heating is formed, using a predetermined polymerization initiator and separating by stirring the unstable raw material mixed solution (stock solution). This stabilized emulsion syrup solution is subjected to UV polymerization, thereby making it possible to obtain an adhesive as a final product.

The size of the hydrophobic domain phase in the adhesive of the present invention can be controlled, for example, by adding a surfactant to the stock solution. Usually, the size of the domain phase depends on the kind of the surfactant, composition (formulation) of the adhesive and technique for conversion into a syrup (e.g. composition of syrup, stirring conditions, polymerization condition, etc.) and is controlled by appropriately selecting these factors.

To easily obtain a stable emulsion, the average diameter of the hydrophobic domain phase is preferably within a range from about 0.04 to about 10 $\mu$m.

Preferably, the starting material for synthesizing the adhesive of the present invention includes:
(1) 2 to 50% by weight of water for forming a hydrophilic phase (this water also functions as a solvent which dissolves a salt for electrolyte solution described hereinafter to form an aqueous electrolyte solution), (2) 5 to 40% by weight of a hydrophobic monomer (may also be a monomer mixture) capable of forming an adhesive hydrophobic polymer in a hydrophobic phase (also referred to as hydrophobic phase), (3) 1 to 40% by weight of a hydrophilic or amphiphatic monomer or oligomer which partially exists in a hydrophilic phase and is capable of forming a hydrophilic polymer, (4) 0.01 to 30% by weight of a surfactant for easily forming a macro- or mini-emulsion, (5) 5 to 50% by weight of a humectant of amino acids, which has a high moisturizing effect, (6) 0.5 to 5% by weight of salts for electrolyte solution, (7) 0.01 to 10% by weight of a plasticizer, (8) 0.01 to 1% by weight of a crosslinking agent, (9) 0.05 to 2% by weight of a water-soluble free-radical photopolymerization initiator, and

(10) 0.005 to 1% by weight of a water-soluble free-radical photopolymerization initiator or an oil-soluble free-radical photopolymerization initiator. The proportion of the above raw material components is selected so that the total amount becomes 100% by weight as far as percentages are by weight.

The hydrophilic polymer is preferably an adhesive polymer. A macro- or micro-emulsion conductive adhesive comprising an adhesive domain phase and a continuous hydrophilic phase can be obtained by selecting the kind and proportion of the monomer or oligomer.

Usually, the hydrophilic phase (also referred to as an aqueous medium) contained in the stock solution contains:
water,
at least one free-radically copolymerizable ethylenically-unsaturated amphiphatic or hydrophilic monomer or oligomer,
salty or salts as an electrolyte, and
a humectant.

The hydrophilic phase can contain other additives, for example, non-reactive polar oligomer additives, free-radically polymerizable photoactivated crosslinking agents, auxiliary solvents, water-soluble free-radical photopolymerization initiators, water-soluble free-radical thermopolymerization initiators, plasticizers and the like.

The hydrophobic phase of the stock solution contains, as a second monomer, a free-radically polymerizable hydrophobic monomer capable of forming a hydrophobic pressure-sensitive adhesive. The hydrophobic phase can contain other arbitrary additives, for example, oil-soluble free-radically photopolymerization initiators, non-reactive polar oligomer additives, oil-soluble crosslinking agents, oil-soluble free-radical thermopolymerization initiators, plasticizers, tackifiers and the like.

The above-described macro- or micro-emulsion can be formed by utilizing a high-speed stirrer, a homogenizer, etc. without using a surfactant. Preferably, a nonionic, anionic, cationic or amphoteric surfactant is used. A reactive surfactant having an ethylenically-unsaturated bond can also be used.

To form a stable macro- or micro-emulsion structure, a stock solution comprising the components other than the crosslinking agent and water-soluble polymerization initiator among the above-described raw material components is prepared first, and the stock solution is subjected to a polymerization treatment to polymerize all or portion of the hydrophobic monomer to form a precursor syrup solution. Other components are usually mixed in a reactor and subjected to a polymerization treatment in the same reactor with stirring.

A stable domain phase having a diameter within a predetermined range can be maintained for a long period of time (usually several hours or more) by such an operation for forming a syrup. The average diameter of the domain in the opaque syrup solution thus obtained is usually measured by a laser scattered particle analyzer. Specific examples of the measuring device include a laser scattered particles analyzer LS230 (model No.) manufactured by Coulter Co.

The above-described crosslinking agent and water-soluble polymerization initiator are added to the syrup solution as a post additive. The syrup solution obtained by adding the post additive is poured into a mold and then subjected to a polymerization treatment. In such a manner, an adhesive as a fmal product can be obtained. Alternatively, a layer of a conductive adhesive can also be formed by coating the syrup solution containing the post additive with a substrate to form a film, followed by a polymerization treatment. A porous substrate such as sheet or mesh sheet containing scrim is impregnated with the syrup solution containing the post additive and then subjected to a polymerization treatment, thereby making it possible to obtain an adhesive sheet, into which the substrate is incorporated as a reinforcing material.

One advantageous effect of the present invention is that an ion conductive adhesive comprising a domain phase containing stably a hydrophobic adhesive polymer in a continuous hydrophilic conductive phase containing a comparatively large amount of a humectant having a high moisturizing effect can be easily produced. According to the present invention, the limitation about the formulation of the respective components is substantially removed, thereby making it possible to form and to maintain a stable macro- or micro-emulsion structure even when a comparatively large amount of a humectant selected from amino acids having a high moisturizing effect.

Hydrophilic Phase

The hydrophilic phase usually contains water in the amount within a range of about 2 to about 50% by weight, and preferably from about 25 to about 40% by weight, based on the total weight of the conductive adhesive. When the amount of water contained in the hydrophilic phase is too small, the moisturizing performance and conductivity are likely to be lowered. On the other hand, when the amount is too large, the cohesive force is lowered and the adhesion property is likely to be lowered. Water is preferably deionized water.

Hydrophilic Polymer

The hydrophilic polymer may be those having no adhesion property. However, those having adhesion properties are preferred for the following reason. In case where the conductive adhesive has a macro- or micro-emulsion structure comprising a domain phase containing a hydrophobic adhesive polymer, and a continuous phase containing a hydrophilic adhesive polymer, both the adhesion strength on initial bonding can be enhanced. Since both of the hydrophobic and hydrophilic adhesive polymers are contained in different phases, the adhesion property is not lowered when the adhesion condition varies, for example, in case where the skin in contact with the adhesive causes sweating or where body exudate such as body fluid effuses from the skin.

The hydrophilic polymer is a polymer of a hydrophilic monomer or oligomer. For example, the first monomer as a raw material of an adhesive, which is contained in the aqueous medium of the stock solution, is substantially composed of a hydrophilic monomer.

The hydrophilic monomer or oligomer (hereinafter referred to as a "hydrophilic monomer") is selected from the group consisting of an oil-insoluble polar monomer or oil-insoluble polar oligomer, which is substantially insoluble in a hydrophobic phase, and a polar monomer or oligomer (having both water-solubility and oil-solubility) other than the oil-insoluble monomer and oligomer. The content of the hydrophilic monomer contained in the stock solution is usually from about 1 to about 40% by weight, and preferably from about 2 to about 20% by weight, based on the total weight of the stock solution.

Preferably, the water-insoluble polar monomer which can be used in as the hydrophilic monomer, includes, for example, polyethylene oxide acrylate, polyethylene oxide diacrylate, polyethylene glycol acrylate, polyethylene glycol diacrylate, polyethylene urethane acrylate, polyethylene urethane diacrylate, acrylamide, sodium styrene sulfonate, sodium acrylate, sodium 2-acrylamide-2-methylpropane sulfonate, sodium methacrylate, and a mixture thereof.

The hydrophilic monomer, which includes polyethylene oxide acrylate or polyethylene oxide diacrylate, preferably, and includes polyethylene oxide acrylate, particularly preferably, is effective for easily forming an adhesive hydrophilic polymer and enhancing the adhesion property of the adhesive containing the same.

The oil-insoluble monomers are preferably those which have the solubility of about 0.5% by weight or less in oil (i.e. hydrophobic phase) and exhibit a distribution ratio (of the concentration in a hydrophobic phase to that in a hydrophobic phase) of about 0.005 or less. The solubility and concentration are values measured at a service temperature (usually about 25 to 35° C.) of the adhesive.

Various known polar monomers are so-called amphiphatic monomers which exhibit a fixed solubility in both water and oil. Such an amphiphatic polar monomer has the solubility of about 0.5% by weight or more in the hydrophobic phase and exhibits the distribution ratio (of the concentration in the hydrophobic phase to that in the hydrophobic phase) of about 0.005 or more (at about 25 to 30° C., usually). These monomers, which can be dissolved in both phases, can be used in combination with the oil-insoluble polar monomer. Useful monomers which can be used in the present invention and partitioned between the hydrophilic phase and hydrophobic phase includes, for example, N-vinyl pyrroldione, N-vinyl caprolactam, (meth)acrylic acid, hydroxyethyl (meth)acrylate, itaconic acid, styrenesulfonic acid, N-substituted acrylamide, N,N-disubstituted acrylamide, N,N-dimethylaminoethyl methacrylate, 2-acrylamide-2-methylpropanesulfonic acid, and a mixture thereof.

Preferred partitionable monomers include acrylic acid, N-vinyl pyrrolidone, N-vinyl caprolactam, N,N-dimethylacrylamide and a mixture thereof because of preferred effect capable of improving the physical strength (e.g. cohesive force of adhesive, etc.).

The hydrophilic phase of the conductive adhesive can further contain various water-soluble additives. Various additives are appropriately selected to exhibit desired characteristics. For example, an electrolyte is added to exhibit the conductivity. To enhance the moisturizing effect, a humectant is added. Examples of the other useful additives include, but are not limited to, water-soluble crosslinking agents (e.g. triethylene glycol dimethacrylate, etc.), water-soluble plasticizers, pH adjustors, non-copolymerizable polar oligomers and mixtures thereof.

Preferably, the electrolyte includes, for example, potassium chloride, lithium chloride, sodium chloride or mixtures thereof. The content of the electrolyte is usually within a range from about 0.1 to about 10% by weight, preferably from about 0.5 to about 5% by weight, and particularly preferably from about 0.8 to about 1.6% by weight, based on the total weight of the adhesive. When the content is within the above range, the electrolyte dissolves in water contained in the hydrophilic phase to effectively function as an aqueous electrolyte solution.

The water-soluble plasticizer is preferably added as an additional component because the adhesion to the skin is enhanced. The content of the plasticizer is usually within a range from about 0.01 to about 10% by weight, and preferably from about 0.5 to about 5% by weight, based on the total weight of the adhesive. When the content of the plasticizer is too large or too small, there is a fear that a desired effect is not obtained. The water-soluble plasticizer includes, for example, those selected from the group consisting of poly(N-vinyl pyrrolidone), polyethylene glycol, poly(oxyethylene) alcohol, polyethylimine and a mixture thereof, but is not limited thereto.

Humectant

As the humectant, for example, polyhydric alcohols such as glycerin, propylene glycol, etc. and amino acids can be used. Preferably, amino acids having a higher moisturizing effect are used. Since the phase structure is not broken when a large amount of the amino acids having a higher moisturizing effect than that of glycerin and propylene glycol are used, there can be provided a biomedical electrode which is hardly dried even when stored under a low-moisture condition outside a sealed pouch. The biomedical electrode using the conductive adhesive containing amino acids can be effectively prevented from drying for a long period of time in a sealed pouch resealed by using a sealing means after opening the sealed pouch under a low-humidity condition. The content of the humectant is usually within a range from about 5 to about 50% by weight, preferably from about 10 to about 40% by weight, and more preferably from about 15 to about 37% by weight, based on the total weight of the adhesive.

Preferably, the humectant includes, for example, amino acids having a higher moisturizing effect than that of glycerin such as trimethylbetaine, DL-pyrrolidonecarboxylic acid (PCA), sodium DL-pyrrolidonecarboxylate, etc. The amino acids are particularly superior in effect of preventing drying of the adhesive.

Specific examples of trimethylbetaine which is useful as the humectant include, for example, Aquadew™ AN-10 which is commercially available from Ajinomoto Co. Specific examples of sodium DL-pyrrolidonecarboxylate include "PCA soda" and "PCA" both of which are commercially available from Ajinomoto Co.

Water-soluble Polymerization Initiator

The aqueous medium of the stock solution preferably contains a water-soluble free-radical photopolymerization initiator. Useful photopolymerization initiator is a water-soluble compound which acts as an initiator for polymerization reaction of a monomer or oligomer (those containing a polymerizable surfactant described below) contained in the stock solution, thereby to form a free radical on exposure to electromagnetic wave (usually ultraviolet light).

Useful water-soluble photopolymerization initiators includes, for example, those selected from the group consisting of benzophenone substituted with an ionic group and/or a hydrophilic group; thoxanthone substituted with an ionic group and/or a hydrophilic group; and phenyl ketone such as 4substituted-(2-hydroxy-2-propyl)phenyl ketone (wherein 4-substituent is an ionic group or a hydrophilic group). Preferably, the ionic group or hydrophilic group include those selected from the group consisting of hydroxyl groups, carboxyl groups and carboxylate groups.

Useful water-soluble benzophenones include, for example, those selected from 4-trimethylaminomethylbenzophenone hydrochloride, benzophenone sodium 4-methanesulfonate and benzophenone sodium 4methanesulfonate. Useful water-soluble thioxanthones include, for example, those selected from the group consisting of 3-(2-hydroxy-3-trirethylaminopropozy) thioxanthone hydrochloride, 3-(3-trimethylaminopropozy) thioxanthone hydrochloride, thioxanthone 3-(2-ethoxysulfonic acid) sodium salt and 3-(3-propoxysulfonic acid) sodium salt. Useful water-soluble phenyl ketones include, for example, those selected from the group consisting of phenyl ketone, (2-hydroxy-2-propyl)(phenyl-4-butanecarboxylate)ketone, 4-(2-hydroxyethoxy)(phenyl-2-propyl)ketone and water-soluble salts thereof. As far as the effect of the present invention is not adversely affected, water-soluble photopolymerization initiators are not limited thereto. Particularly preferred water-soluble photopolymerization initiator is 1-(4-(2-hydroxy)-phenyl)-2-2-hydroxy-2-ethyl-propan-1-one).

The above-described water-soluble photopolymerization initiator can be contained in the aqueous medium in a different amount depending on the desired effect. The content of the water-soluble photopolymerization initiator is usually within a range from about 0.05 to about 2% by weight, and preferably from about 0.1 to about 1% by weight, based on the total weight of the stock solution.

Hydrophobic Phase

The hydrophobic phase contains a hydrophobic adhesive polymer or copolymer. In the present specification, these polymer and copolymer are generically referred to as a "hydrophobic adhesive polymer." The hydrophobic adhesive polymer is usually a polymer of the second monomer (including a monomer mixture), comprising a hydrophobic free-radically polymerizable monomer and a free-radically polymerizable polar monomer. As the hydrophobic free-radically polymerizable monomer, for example, one or more kinds of them can be selected from alkyl(C1–C18) alcohol ester of acrylic acid. It is selected so that the polymer produced from these monomers is an adhesive polymer. The glass transition temperature (Tg) of a useful hydrophobic free-radically polymerizable monomer (including a mixture) can be measured by a person with ordinary skill using a known technique. Tg is usually 10° C. or less, preferably 0° C. or less, and particularly preferably −10° C. or less.

Preferred hydrophobic free-radically polymerizable monomers include, for example, one or more kinds selected from isooctyl acrylate, 2-ethylhexyl acrylate and n-butyl acrylate.

To produce the hydrophobic adhesive polymer, the hydrophobic second monomer contained in the stock solution optionally contains a free-radically polymerizable polar monomer, which is copolymerizable with an alkyl acrylate, to control Tg of the adhesive polymer within a preferred range. Preferred polar monomer includes, for example, styrene, acrylonitrile and vinyl ester (e.g. vinyl acetate, vinyl propionate, vinyl neopentanoate, etc.).

The content of the hydrophobic second monomer is usually within a range from about 5 to about 40% by weight, preferably from about 7 to about 30% by weight, and particularly preferably from about 10 to about 20% by weight, based on the total weight of the stock solution so as to easily impart sufficient cohesive force and adhesion property to the conductive adhesive as a polymerization product form the stock solution.

Oil-soluble Polymerization Initiator

To easily control the polymerization of the second monomer, the stock solution preferably contains an oil-soluble free-radical photopolymerization initiator (photopolymerization initiator) and/or an oil-soluble free-radical thermopolymerization initiator (thermal polymerization initiator).

Useful oil-soluble photopolymerization initiators are oil-soluble compounds which act as an initiator for polymerization reaction of a monomer or oligomer (those containing a polymerizable surfactant described below) contained in the stock solution, thereby to form a free radical on exposure to electromagnetic wave (usually ultraviolet light).

Useful oil-soluble photopolymerization initiators include, for example, those selected from the group consisting of (1) Michler's ketone and benzophenone mixed in a weight ratio of about 1:4; (2) coumarin-based photopolymerization initiator described in U.S. Pat. No. 4,289,844; and (3) photopolymerization initiator containing dimethoxyphenylacetophenone and/or diethoxyacetophenone as a base. A preferred photopolymerization initiator is 1-hydroxy-cyclohexyl phenyl ketone.

The oil-soluble initiator is an oil-soluble compound which is originally contained in the hydrophobic phase of the stock solution and forms a free radical on polymerization operation (e.g. UV irradiation, etc.), said free radical capable of allowing to proceed the polymerization of the monomer.

Specific examples of the oil-soluble thermal polymerization initiator which can be used in place of or in combination with the photopolymerization initiator include, for example, azo compounds such as "trade name: Vazo 64, 2,2'-azobis (isobutyronitrile)" or "trade name: Vazo 52, 2,2'-azobis(2, 4-dimetyhylpentanenitrile)" (both of which are commercially available from DuPont Co.). A peroxide such as benzyl peroxide, lauroyl peroxide and a mixture thereof can also be used. Preferred oil-soluble thermal polymerization initiator is 2,2'-azobis(isobutyronitrile).

The content of the water-soluble initiator (content of a mixture when using the photopolymerization initiator in combination with the thermal polymerization initiator) is usually within a range from about 0.005 to about 1% by weight, and preferably from about 0.01 to about 0.1% by weight, based on the total weight of the stock solution.

Hydrophobic Additive

The hydrophobic phase of the stock solution can optionally contain an additional free-radically reactive additive such as oil-soluble crosslinking agent. Examples of useful crosslinking agent include those selected from the group consisting of divinylbenzene, alkyl (about C4–C8) diacrylate, 1,4-hexanediol diacrylate, 1,8-octanediol diacrylate and a mixture thereof, but are not limited thereto. Preferred crosslinking agent is 1,6-hexanediol diacrylate. When the crosslinking agent is added, the physical characteristics of the final polymer, for example, cohesive force, insolubility to solvent, elasticity modulus, etc. are improved. The hydrophobic phase usually contains the crosslinking agent in the amount within a range from about 0.01 to about 10% by weight, preferably from about 0.02 to about 1% by weight, and particularly preferably from about 0.05 to about 0.2% by weight, based on the total weight of the stock solution.

Surfactant

The surfactant used preferably for preparing the conductive adhesive of the present invention may also be a reactive surfactant, which is copolymerizable or not copolymerizable with the above monomer, and can be used properly depending on the purpose. In the case of the reactive surfactant, for example, the sensitivity of the conductive adhesive to water is lowered, thereby making it possible to easily prevent the adhesion property from drastically lowering due to an influence of sweating.

The surfactant which can be usually used includes, for example, nonionic surfactants, cationic surfactants, or anionic surfactants. The content of the surfactant is usually within a range from about 0.01 to about 30% by weight, and preferably from about 5 to about 20% by weight, based on the total weight of the adhesive.

The nonionic surfactant may be usually an organic aliphatic or alkyl aromatic hydrophobic compound, and a condensation product of a hydrophilic alkylene oxide such as ethylene oxide. Almost all of hydrophobic compounds having a carboxy, hydroxy, amido or amino group with liberation of hydrogen are condensed with ethylene oxide to form a nonionic surfactant. A desired balance between hydrophobic and hydrophilic elements (hydrophilicity— lipophilicity balance or HLB) is attained by controlling the length of an ethylene oxide chain of the codensate. HLB of the surfactant can be controlled by the size or kind of a hydrophilic (water-loving or polar) group and a lipophilic (oil-loving or non-polar) group of the surfactant. HLB of the nonionic surfactant is usually from about 6 to about 19.

Useful noninic surfactants include, for example, those selected from the group consisting of non-copolymerizable nonionic surfactant, ethylenically-unsaturated copolymerizable nonionic surfactant and a mixture thereof.

The anionic surfactant usually includes:
(a) a hydrophobic moiety selected from the group consisting of C6–C20 alkyl group, alkylaryl group and alkenyl group, and
(b) a hydrophilic moiety comprising an anionic group selected from the group consisting of sulfate, sulfonate, phosphonate, polyoxyethylene sulfate, polyoxyethylene sulfonate, polyoxyethylene phosphonate and alkali metal and ammonium salts thereof, or tertiary amino salt group of these anionic groups.

A copolymerizable surfactant comprising C2–C18 alkenyl polyoxypropylene or C2–C18 polyoxybutylene as the hydrophobic moiety, an anionic group of polyoxyethylene sulfate as the hydrophilic moiety, and an ethylenically-unsaturated double bond is also useful.

To obtain a more stable macro- or micro-emulsion, an ethylenically-unsaturated polymerizable anionic surfactant is preferred. Specific examples of the copolymerizable anionic surfactant include Mazonm™ SAM 211 which is commercially available from PPG Industries Inc. and Adekareasor™ SE-10N (product No.): ammonia salt of α-sulfo-χ{1-nonylphenoxymethyl-2-(2-propenyloxy)ethoxy} -poly(oxy-1,2-ethanediyl) manufactured by Assahi Denka Kogyo Co.

The non-reactive surfactant is preferably sodium polyoxyethylene alkyl(C10–C16) ether sulfates such as Emale™ E-27C, Emale™ E-70C, etc., which are commercially available from Kao Corp.

As the cationic surfactant, for example, there can be used quaternary ammonium salts wherein at least one higher molecular weight groups (having 6 or more carbon atoms) and two or more lower molecular weight groups (having 1 to 5 carbon atoms) are linked to a common nitrogen atom to produce a cation, resulting in electrical balance. In this case, the anion includes those selected from the group consisting of halide (e.g. bromide, chloride, etc.), acetate, nitrate and lower alkosulfate (e.g. methosulfate, etc.), but are not limited thereto.

Precursor syrup

The above macro- or micro-emulsion structure is not formed easily and is preferably formed in the following procedure.

First, components other than the crosslinking agent and water-soluble polymerization initiator among the raw material components are charged in a UV reactor or thermal reactor, and then mixed with purging a nitrogen gas in the reactor. When using the photopolymerization initiator, the raw material mixture in the reactor is polymerized by UV irradiation. The UV intensity of a UV lamp for UV irradiation is from 0.1 to 10 mW/cm$^2$. When using the thermal polymerization initiator, the mixture is polymerized by heating.

Usually, the polymerization treatment is conducted with stirring and the polymerization treatment is conducted until the domain structure containing the hydrophobic adhesive polymer is fixed, that is, stabilized. The end point of the formation of the precursor syrup solution is decided by the viscosity of the emulsion containing the domain phase. Preferred viscosity is from 100 to 4000 cps.

On the other hand, the respective components are preferably used in the amount within the above range. It is particularly preferred that the amount of water, and kind and amount of the humectant are decided, and then the amount of other components is decided so as to obtain desired characteristics. Water and humectant are important factors to control the initial amount of water contained and retained, and the amount of water contained in the adhesive is a principal factor which exerts a great influence on the conductivity and adhesion property.

The step of deciding the composition is now described with reference to a specific example. For example, 1.5 parts by weight of an electrolyte is dissolved in 36 parts by weight of water to prepare an electrolyte solution. Then, 22 parts by weight of the above-described humectant of amino acids is added as the humectant so as to attain a water retention (percentage) of about 10% under the conditions of 20° C.-20% RH (relative humidity).

The formulation of the respective components is decided so that the total amount of the hydrophobic monomer, hydrophilic monomer and water-soluble plasticizer becomes 40 parts by weight based on 59.5 parts by weight of the above components. This formulation ratio is decided so that the physical properties such as adhesion property, flexibility, etc. are within the desired range. When using the amphiphatic monomer, the amount may be controlled to 40 parts including the amount of the monomer. Furthermore, 0.05 parts by weight of an oil-soluble photopolymerization initiator is dissolved to obtain a mixed solution of the total amount of 100 parts by weight.

The above mixed solution is a white turbid emulsion during the stirring, but is separated when the stirring is terminated. To form a more stable emulsion, a predetermined amount of the surfactant is added to about 100 parts by weight of the above mixed solution so that the resulting solution is a uniform opaque liquid during the stirring and is not separated soon even when the stirring is terminated. The amount of the surfactant varies depending on the kind of the surfactant and incorporation of components other than the surfactant, but is preferably from 5 to 20 parts by weight.

In such way, the above comparatively stable emulsion is obtained as the stock solution. Subsequently, this stock solution is irradiated with UV with stirring to obtain a precursor syrup solution as an adhesive precursor of a stable emulsion. Then, 0.1 parts by weight of a crosslinking agent and 0.5 parts by weight of a water-soluble photopolymerization initiator are added to the resulting syrup solution, and the mixture is irradiated with UV to obtain an adhesive composition of the present invention as a final product. The amount of the above respective components can be controlled to satisfy the require characteristics by repeating tests.

Formation of Conductive Adhesive Layer

After a macro- or micro-emulsion was once formed by the above method for conversion into a syrup, a final product, i.e. a conductive adhesive of the present invention can be obtained by polymerization of the emulsion in accordance with a known procedure.

For example, the precursor syrup solution obtained as described above is coated on a proper substrate by using a conventional means such as roller coating, dip coating, knife coating, extrusion coating, etc. to form a layer of the precursor-syrup solution. At this time, a water-soluble polymerization initiator, and a crosslinking agent to be added optionally are added to the precursor syrup solution.

Then, the formed layer of the precursor syrup solution (hereinafter referred to as a syrup layer) is polymerized in an inert atmosphere (in a state free from oxygen, e.g. under a nitrogen atmosphere) to form an adhesive layer of a conductive adhesive. For example, UV irradiation is conducted under anaerobic conditions by laying a plastic film, which is substantially permeable to ultraviolet light but impermeable to oxygen, on the syrup layer, thereby to cause the polymerization reaction. UV irradiation can be usually conducted through the plastic film, using a fluorescent type ultraviolet lamp which emits ultraviolet light in a wavelength range absorbed by a UV photopolymerization initiator. The plastic film used herein is preferably a polyester film whose surface to be made in contact with the syrup layer is a silicone release surface.

UV irradiation can be preferably conducted by using a plurality of commercially available different lamps. Examples of the lamp include combination of low-pressure mercury lamp or medium-pressure mercury lamp and low-intensity fluorescent lamp. In this case, each lamp has a different emission spectrum and emits light having a maximum intensity within a range from 280 to 400 nm. Usually, a commercially available black lamp, which has a maximum of the intensity at about 350 nm and shows 90% of the intensity distribution within a range from 300 to 400 nm, is used.

The total dose on UV irradiation is usually from about 200 to 5000 millijoules (mJ)/cm². Usually, the efficiency and rate of polymerization is decided by the relation between emission properties of an irradiation light source and absorption characteristics of the UV photopolymerization initiator.

Preferred photopolymerization process is a process of continuously exposing the syrup layer to electromagnetic wave of about 350 nm for enough time to provide the dose of about 2000 mJ/cm².

The thickness of the conductive adhesive layer varies depending on the state on use, but is from about 0.1 to about 4 mm, and preferably from about 0.5 to about 2 mm. When the thickness of the conductive layer is too small, the anti-drying performance is likely to be lowered. On the other hand, when the thickness is too large, the volume of whole biomedical electrode becomes large, resulting in poor handling.

UV irradiation can be conducted from one surface of the syrup layer, but is preferably conducted from both surfaces. In the syrup layer having a thickness of 0.8 mm or more, the syrup is white or opaque and, therefore, the light scattering effect in the emulsion can not be neglected. Accordingly, irradiation from both surfaces is preferred so that both surfaces of the adhesive layer have the same properties.

Biomedical Electrode

A biomedical electrode comprising an adhesive layer of the conductive adhesive is particularly useful for diagnosis (including monitoring) and treatment in the medical field. In a basic form, the biomedical electrode comprises an electrode terminal which is made contact with the skin of mammals (including human) as a patient or subject, thereby making it possible to form mutual electrical communication between a conductive adhesive layer and an electrical diagnostic, therapeutic or electrosurgical equipment.

Figure 2:
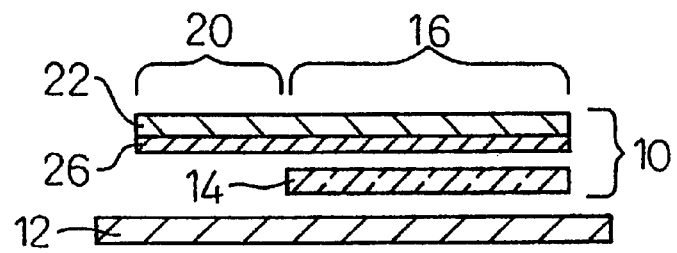
FIG. 2 is a cross-sectional view showing a configuration of the biomedical electrode shown in FIG. 1.

FIG. 1 and FIG. 2 each shows one preferred embodiment of the biomedical electrode according to the present invention. The biomedical electrode shown in the drawing is disposable and can be applied to the skin of the patient on use so as to obtain an electrocardiogram (ECC or EKG) or to afford a transcutaneous electrical nerve stimulation (TENS).

A biomedical electrode 10 shown in the drawing comprises a field of a conductive adhesive layer to be made in contact with the patient's skin on removal of a release liner 12 for protection of the adhesive layer (hereinafter referred to as a conductive field) 14, an electrical connection means 16 including a conductive film 26 having a conductive interface portion, which is made contact with the conductive field 14, and a tab portion 20 for mechanical or electrical connection with an electrical instrumentation (not shown), which extends beyond the conductive field 14. The electrical connection means 16 finctions as an electrode terminal. The electrical connection means 16 includes a substrate 22, and a conductor film 26 coated on a principal surface made in contact with at least conductive field 14 of the substrate.

The typical conductor film 26 includes a substance having a thickness of about 0.05 to 0.2 mm, e.g. strip of a polyester film, and has a silver/silver chloride coating layer having a thickness of about 2.5 to 12 $\mu$m, (preferably about 5 $\mu$m) thereon. Specific examples of the conductor film 26 include coating layer of conductive ink, i.e. silver/silver chloride ink R-300 (product No.) which is commercially available from Ercon Co. The electrical connection means 16 can be obtained, for example, by providing this coating layer on a principal surface of a polyester film substrate which is commercially available from 3M Co. under the trade name of "Scotchpar™" or which is commercially available from ICI Co. under the trade name of "Melinex™" 505–300, 329 or 339.

The electrical connection means 16 of the biomedical electrode for TENS comprises a non-woven fabric such as fabric of polyester/cellulose fibers which is commercially available from Lydal Co. under the trade name of "Mannlweb™", and has a conductor film of a carbon ink layer which is commercially available from Acheson Coiloids Co. under the trade name of Carbon Ink SS243 63 (product No.) on the principal surface.

To enhance mechanical contact between an electrode clip (not shown) and the conductor film 16, an adhesive tape with a substrate of polyethylene can be applied to the tab portion 20 located on the surface opposite the principal surface having a conductive coating 26. As the adhesive tape, a surgical tape, which is commercially available from 3M Co. under the trade name of "Blenderm™", can be used.

A conductor comprising a non-conductive flexible polymer film and a conductive layer having a multi-layer structure as disclosed in International Publication WO9741568 can be used selectively as the above electrical connection means. This conductor has a conductive layer composed of a base conductive layer having small porosity, which is formed by coating conductive ink containing a hydrophobic polymer binder, silver particles and carbon particles on a polyester film, and a top conductor layer having large porosity, which is formed by coating conductive ink containing a polymer binder, Ag/AgCl particles and carbon particles on the base conductive layer.

Figure 3:
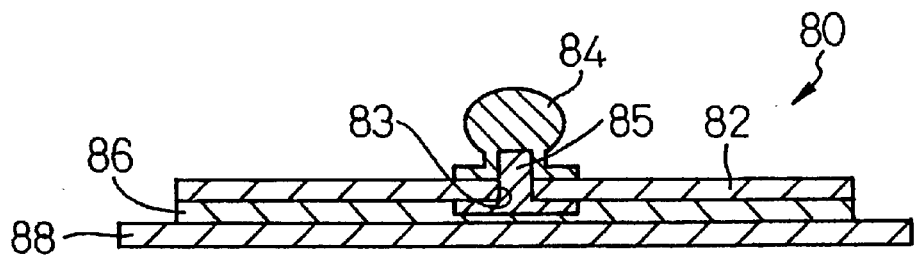
FIG. 3 is a planar view showing another preferred embodiment of a biomedical electrode according to the present invention.

A biomedical electrode having another structure is shown in FIG. 3 as a cross-sectional view. A biomedical electrode 80 shown in the drawing includes a non-conductive coating 82 having an opening 83 covered by a snap 84 through which an electrode terminal including an eyelet 85 protrudes. The snap 84 is fixed to coat the eyelet 85, thereby to give electrical connection with an electrical instrumentation. The eyelet 85 is electrically connected with a conductive adhesive layer 86, and the adhesive layer 86 of the conductive adhesive of the present invention is perfectly coated with the snap 84 and the non-conductive coating 82.

A release liner 88 is used for protecting the adhesive layer 86 before use. The non-conductive coating 82 is usually made of an insulating substance. The eyelet 85 is, for example, an eyelet made of a plastic metal plate. Such an eyelet is, for example, an ABS plastic eyelet made of a silver plate or a chloride, and is commercially available from Micron Products Co. The snap 84 is, for example, a metal snap. Such a snap is, for example, a stainless eyelet which is commercially available from Eyelet for Industry of Thomson under the product No. 304.

Other examples of biomedical electrodes, which can use the conductive adhesive of the present invention, include electrodes disclosed in the following U.S. Pat. Nos. 4,524,087, 4,539,996, 4,554,924, 4,848,353, 4,846,185, 4,771,713, 4,715,382, 5,012,810 and 5,133,356. The method of producing these electrodes is not disclosed in each specification, but the conductive adhesive of the present invention can be replaced by the conductive adhesive disclosed herein.

Packaging of Biomedical Electrode

On actual use of the biomedical electrode, a fixed number (e.g. 3, 5 or 10) of biomedical electrodes required for single inspection are applied to one release liner and a fixed number (e.g. 1, 5 or 10) of release liners with biomedical electrodes, on which the required numbers of biomedical electrodes are applied, are put in a sealed pouch made from an aluminum foil and then stored and taken out immediately before use.

In case where the biomedical electrode stored in the sealed pouch is once taken out, put in the sealed pouch again and allowed to stand under a low-humidity condition, it is difficult to store the release liner with the biomedical electrode in a conventional sealed pouch for a long period of time. It is difficult to completely reseal a conventional sealed pouch. Accordingly, a sealed pouch provided with a simple sealing means (e.g. so-called zip lock fastener, etc.) for simply resealing after opening is preferably used to maintain predetermined characteristics (e.g. conductivity, etc.) under a low-humidity condition even after opening of the sealed pouch.

In the biomedical electrode according to the present invention, since a conductive adhesive having a high moisturizing effect in which drying is effectively prevented is used, a liner with a plurality of electrodes is stored in a sealed pouch provided with a simple sealing means after opening and a part of the biomedical electrode can be used in several portions, if necessary.

EXAMPLES

Example 1

(1) Preparation of Precursor Syrup Solution
(Hereinafter Referred to as a "Syrup Number N1")
Composition of Precursor Syrup Solution N1

TABLE 1

| | (N1) | | | |
|---|---|---|---|---|
| | Raw materials | | Parts by weight | % by weight |
| Monomers | UV(Oil) | Irg. 184 | 0.05 | 0.04 |
| | AA | AA | 14 | 12.10 |
| | IOA | IOA | 14 | 12.10 |
| | Surfactant | SE-10N | 17.4 | 15.04 |
| | Aqueous monomer | MPEG550MA | 8 | 6.91 |
| | Plasticizer | PEG300 | 3 | 2.59 |
| Salt solution | Humectant | Aquadew | 22 | 19.01 |
| | 4% KCl | 40% KCL | 37.25 | 32.20 |
| | | Total | 115.7 | 100.000 |

The precursor syrup solution N1 of this example is a micro-emulsion having the above-described composition. The solution was prepared by stirring a mixed solution of raw materials described in Table 1 with subjecting to UV irradiation in a UV reaction vessel equipped with a glass container, a propeller coated with Teflon™, purge line of a nitrogen gas, a vessel cover and a UV lamp. The procedure is generally described below.

The glass container of the UV reaction vessel was filled with the following raw materials:

"Irgacure 184™, 1-hydroxy-cyclohexyl phenyl ketone" manufactured by Ciba Geigy Co. as an oil-soluble UV photopolymerization initiator (UV), isooctyl acrylate (IOA) as a second monomer capable of producing a hydrophobic adhesive polymer, methoxypolyethylene glycol 550 monoacrylate (MPEG550MA, manufactured by Satomer Co.) and acrylic acid (AA) as a first monomer capable of producing an adhesive hydrophilic monomer, and polyethylene glycol 300 (PEG300) as a plasticizer, thereby to obtain a mixed solution.

After stirring at about 100 rpm until Irgacure 184 was dissolved, an aqueous 4% KCl solution and a reactive surfactant Adekareasoap™ SE-10N (product No.) manufactured by Asahi Denka Kogyo Co. were added to the resulting mixed solution. After the dissolution of Adekareasoap was visually confirmed, a humectant Aquadew™ AN-100 (product No.) manufactured by Ajinomoto Co. was further added.

After the dissolution of Aquadew was visually confirmed, a nitrogen gas was purged in the glass container with stirring at 80 rpm. Using a UV lamp controlled so that a measured intensity at the surface of the glass container becomes 2 mW/cm$^2$, UV irradiation was conducted for about 40 seconds until bubbles of the gas evolve slowly. As a result of a series of operations, the appearance of the mixed solution was changed to opaque from transparent. This change means that a precursor syrup solution N1 for preparation of a desired adhesive was formed in this example.

Then, the average diameter of a domain phase of the resulting precursor syrup solution N1 was measured by a laser scattered particles analyzer LS230 (model No.) manufactured by Coulter Inc. As a result, it was 0.2 μm. The viscosity of the precursor syrup solution N1 was measured by a B-M type viscometer. As a result, it was 160 cps at 25° C.

(2) Preparation of Two Kinds of Coating Syrup Solutions (Hereinafter Referred to as "Syrup No. N1-a" and "syrup No. N1-b")

Composition of Coating Syrup Solution N1-a:

TABLE 2

(N1-a)

| Raw materials | | Parts by weight | % by weight |
| --- | --- | --- | --- |
| Precursor | Precursor syrup solution N-1 | 115.7 | 99.53 |
| UV photoinitiator | Irg. 2959 | 0.5 | 0.43 |
| Crosslinking agent | TEGDMA | 0.05 | 0.04 |
| | Total | 116.25 | 100.00 |

Water content: 30.8%

Composition of Coating syrup solution N1-b:

TABLE 3

(N1-b)

| Raw materials | | Parts by weight | % by weight |
| --- | --- | --- | --- |
| Precursor | Precursor syrup solution N-1 | 115.7 | 99.48 |
| UV photoinitiator | Irg. 2959 | 0.5 | 0.43 |
| Crosslinking agent | TEGDMA | 0.1 | 0.09 |
| | Total | 116.3 | 100.00 |

Water content: 30.8%

To the precursor syrup solution N1 thus prepared, raw materials described in Table 2 or Table 3 were added, followed by sufficient mixing. "Irgacure™-2952" {1-(4-(2-hydroxyethoxy)-phenyl)-2-hydroxy-2-methyl-1-propan-1-one} manufactured by Ciba Geigy Co. as a water-soluble UV photopolymerization initiator and triethylene glycol dimethacrylate (TEGDMA) manufactured by Tokyo Chem. Ind. as a crosslinking agent were added, respectively. As a result, coating syrup solutions N1-a and N1-b each having the above composition were obtained. Each coating syrup solution was also an opaque liquid having a mini-emulsion structure.

(3) Preparation of Conductive Adhesive (Adhesive Sheet)

Using a UV coater equipped with a low-pressure TV lamp at top and bottom positions, the coating and curing (crosslinking) of the coating syrup were conducted. First, the coating syrup solutions N1-a and N1-b prepared as described above were coated on a KC tissue Scrim™ manufactured by Kimberly Clark Co. placed on a white double-coated liner in a coating thickness of 1 mm using a knife coater. On coating of each syrup solution, a transparent liner was laminated to contact the surface of the syrup solution with the silicone release surface, and then the syrup solution was coated by placing a knife on the transparent liner.

A power source of top and bottom UV lamps was controlled so as to obtain the same intensity through both liners (white double-coated liner and transparent liner) and the layer of the coating syrup interposed between the liners was cured. The energy integrated on the surface of the coated layer of the syrup solution was 1050 mJ/cm$^2$ per one surface.

After the completion of the curing treatment due to UV irradiation, a conductive adhesive interposed between both liners of this example was obtained. That is, an adhesive sheet comprising a reinforcing substrate of the above scrim and an adhesive layer of a conductive adhesive with which the reinforcing substrate is impregnated of this example was obtained. In this state, the obtained one has a form of an adhesive sheet with double-coated liner wherein both adhesive surfaces are protected with the double-coated liner. This adhesive sheet with the double-coated liner is adhered to a backing film after peeling off one liner, thereby making it possible to use as a conductive adhesive film having a three-layer structure of backing film/adhesive sheet/liner.

After the adhesive sheet with the double-coated liner prepared as described above was stored in a vinyl bag for one day, the thickness of the adhesive sheet was measured. As a result, it was 0.8 to 0.9 mm. The residual monomer of the adhesive sheet was analyzed by a gas chromatography (GC) and a liquid chromatography (LC). As a result, the residual monomer was not detected. The detection limit was 10 ppm.

(4) Production of Biomedical Electrode

The adhesive sheet of this example was incorporated into a stud type electrode described previously with reference to FIG. 3. Accordingly, this biomedical electrode has a structure of an adhesive sheet (with single-coated liner), a backing of polyethylene and polypropylene, a carbon stud and a Ag/AgCl black eyelet. The adhesive sheet was incorporated by peeling off one liner from the adhesive sheet with the both-coated liner made as described above, and adhering to a backing.

The biomedical electrode made as described above was stored in a sealed pouch made of an aluminum foil, and also stored in a sealed pouch with a zip lock fastener for resealing the opened pouch.

(5) Characteristics Evaluation Test

The characteristics of the biomedical electrode made as described above were evaluated in accordance with the following criteria and procedures.

Lifetime of Electrode

A target of the lifetime of the biomedical electrode may be two years in case where the biomedical electrode is stored in a sealed pouch at room temperature. The present inventors have recognized based on experience that the electrode has the lifetime of two years at room temperature of 20 to 25° C. if the electrode aged at 57° C. for 10 weeks or aged at 66° C. for 6 weeks meets the electrical characteristics defined in the standard of AAMI (Association for the Advancement of Medical Instrument). Accordingly, in the characteristics evaluation test of this example, it was judged whether or not the biomedical electrode can have fixed electrical characteristics and adhesion characteristics even after aging. Furthermore, the adhesion strength to the skin of human as a typical subject was also measured at initial stage and after aging (after 3 weeks and 6 weeks).

Resistance to Drying

A target of the resistance to drying of the biomedical electrode is that the electrode can sufficiently maintain AAMI characteristics during storage under the conditions of 20° C.-20% RH (relative humidity) outside a sealed pouch for 30 days. Accordingly, in the characteristics evaluation test of this example, it was judged whether or not the electrode stored outside the sealed pouch and the electrode, which was put in an opened sealed pouch and then resealed by a zip lock fastener, can have have fixed electrical characteristics and adhesion characteristics even after aging. Furthermore, the adhesion strength to the skin of human as a typical subject was also measured at initial stage and after aging (after 3 weeks and 6 weeks).

The AAMI characteristics refer to proper performances that are determined with respect to a biomedical electrode used in an EGG disposable electrode by AAMI using the following criteria and test procedures. The test procedure and standard with respect to the minimum criteria are composed of the following four items.

| | |
|---|---|
| (1) DC offset potential | 100 mV or less |
| (2) AC impedance | 2000 Ω or less |
| (3) Offset potential after 5 seconds have passed since defibrillation | 100 mV or less |
| (4) Recovery speed after 5 seconds have passed since defibrillation | 0–1.0 mV/s |

(change in residual polarization potential after 5 seconds have passed since 4 charging/discharging)

Accordingly, in the characteristics evaluation test of this example, the evaluation tests for four items described above were carried out by using an ECC electrode tester Xtrateck EF-68ATM (manufactured by Xtrateck Co.). At initial stage and after aging or drying, the respective biomedical electrodes was connected back to back (adhesive-adhesive) with each other to make a pair of test electrodes, and then the measurement was carried out in accordance with a manual described in the tester.

Subsequently, the adhesion test (skin adhesion test) of the adhesive sheet of this example was carried out in the following procedure.

First, the above single-coated liner was laid on a polyester film to make an adhesive film. The resulting film was cut into pieces of 2.54×7.6 cm in size to obtain a strip-like test piece. The resulting test piece was placed on the subject's chest and applied uniformly by rolling a roller of 1 kg. Using a mechanical peeling device referred to as an adhesion tester, the test piece was peeled off immediately before application. The peeling condition of the strip was as follows: speed of 12 inch/min and a direction of 180 degree. Each adhesion strength (adhesion force) was recorded by the number of gram per 2.54 cm (1 inch) [g/2.54 cm].

As a result of a series of characteristics evaluation tests as described above, the measurement results described in Table 4 to Table 9 were obtained.

TABLE 4

Aging stability of a stud type biomedical electrode derived from a coating syrup solution N1-a in a sealed pouch at 66° C.

| Tests | AAMI specification | Initial | 3 weeks | 6 weeks |
|---|---|---|---|---|
| DC offset potential | 100 mV or less | 0.1 mV | −0.2 mV | −0.3 mV |
| AC impedance | 2000 Ω or less | 198 Ω | 203 Ω | 188 Ω |
| Offset potential after 5 seconds have passed since defibrillation | 100 mV or less | 10.2 mV | 11.2 mV | 12.1 mV |
| Recovery speed after 5 seconds have passed since defibrillation | 0 to −1.0 mV/s | −0.2 mV/s | −0.3 mV/s | −0.3 mV/s |
| Adhesion strength of stud type electrode | 100 to 400 g per each electrode | 215 g per each electrode | 290 g per each electrode | 290 g per each electrode |

TABLE 5

Aging stability of a stud type biomedical electrode derived from a coating syrup solution N1-b in a sealed pouch at 66° C.

| Tests | AAMI specification | Initial | 3 weeks | 6 weeks |
|---|---|---|---|---|
| DC offset potential | 100 mV or less | −0.2 mV | −0.3 mV | 0.5 mV |
| AC impedance | 2000 Ω or less | 251 Ω | 213 Ω | 183 Ω |
| Offset potential after 5 seconds have passed since defibrillation | 100 mV or less | 11.1 mV | 11.2 mV | 12.7 mV |
| Recovery speed after 5 seconds have passed since defibrillation | 0 to −1.0 mV/s | −0.2 mV/s | −0.3 mV/s | −0.3 mV/s |
| Adhesion strength of stud type electrode | 200 to 400 g per each electrode | 180 g per each electrode | 255 g per each electrode | 320 g per each electrode |

TABLE 6

Resistance to drying of a stud type biomedical electrode derived from a coating syrup solution N1-a under 20° C.-20% RH outside a sealed pouch

| Tests | AAMI specification | Initial | 10 days | 20 days | 30 days |
|---|---|---|---|---|---|
| DC offset potential | 100 mV or less | 0.1 mV | 0.0 mV | −0.5 mV | −0.4 mV |
| AC impedance | 2000 Ω or less | 198 Ω | 427 Ω | 1009 Ω | 1756 Ω |
| Offset potential after 5 seconds have passed since defibrillation | 100 mV or less | 10.2 mV | 11.8 mV | 13.7 mV | 16.7 mV |
| Recovery speed after 5 seconds have passed since defibrillation | 0 to −1.0 mV/s | −0.2 mV/s | −0.3 mV/s | −0.3 mV/s | −0.5 mV/s |

TABLE 6-continued

Resistance to drying of a stud type biomedical electrode derived from a coating syrup solution N1-a under 20° C.-20% RH outside a sealed pouch

| Tests | AAMI specification | Initial | 10 days | 20 days | 30 days |
|---|---|---|---|---|---|
| Adhesion strength of stud type electrode | 100 to 400 g per each electrode | 215 g per each electrode | 360 g per each electrode | 375 g per each electrode | 475 g per each electrode |

TABLE 7

Resistance to drying of a stud type biomedical electrode derived from a coating syrup solution N1-b under 20° C.-20% RH outside a sealed pouch

| Tests | AAMI specification | Initial | 10 days | 20 days | 30 days |
|---|---|---|---|---|---|
| DC offset potential | 100 mV or less | −0.2 mV | 1.5 mV | 0.2 mV | −0.1 mV |
| AC impedance | 2000 Ω or less | 251 Ω | 445 Ω | 831 Ω | 1878 Ω |
| Offset potential after 5 seconds have passed since defibrillation | 100 mV or less | 11.1 mV | 11.7 mV | 13.3 mV | 16.1 mV |
| Recovery speed after 5 seconds have passed since defibrillation | 0 to −1.0 mV/s | −0.2 mV/s | −0.3 mV/s | −0.3 mV/s | −0.4 mV/s |
| Adhesion strength of stud type electrode | 100 to 400 g per each | 215 g per each electrode | 415 g per each electrode | 440 g per each electrode | 460 g per each electrode |

TABLE 8

Resistance to drying of a stud type biomedical electrode derived from a coating syrup solution N1-a under 20° C.-20% RH outside a sealed pouch (resealed by zip lock fastener)

| Tests | AAMI specification | Initial | 20 days | 30 days |
|---|---|---|---|---|
| DC offset potential | 100 mV or less | 0.1 mV | 0.1 mV | −0.4 mV |
| AC impedance | 2000 Ω or less | 198 Ω | 303 Ω | 247 Ω |
| Offset potential after 5 seconds have passed since defibrillation | 100 mV or less | 10.2 mV | 10.8 mV | 10.1 mV |
| Recovery speed after 5 seconds have passed since defibrillation | 0 to −1.0 mV/s | −0.2 mV/s | −0.2 mV/s | −0.2 mV/s |
| Adhesion strength of stud type electrode | 100 to 400 g per each electrode | 215 g per each electrode | 235 g per each electrode | 200 g per each electrode |

TABLE 9

Resistance to drying of a stud type biomedical electrode derived from a coating syrup solution N1-b under 20° C.-20% RH outside a sealed pouch (resealed by zip lock fastener)

| Tests | AAMI specification | Initial | 20 days | 30 days |
|---|---|---|---|---|
| DC offset potential | 100 mV or less | −0.2 mV | −0.2 mV | −0.3 mV |
| AC impedance | 2000 Ω or less | 251 Ω | 202 Ω | 257 Ω |
| Offset potential after 5 seconds have passed since defibrillation | 100 mV or less | 11.1 mV | 10.3 mV | 10.6 mV |
| Recovery speed after 5 seconds have passed since defibrillation | 0 to −1.0 mV/s | −0.2 mV/s | −0.2 mV/s | −0.2 mV/s |

TABLE 9-continued

Resistance to drying of a stud type biomedical electrode derived from a coating syrup solution N1-b under 20° C.-20% RH outside a sealed pouch (resealed by zip lock fastener)

| Tests | AAMI specification | Initial | 20 days | 30 days |
|---|---|---|---|---|
| Adhesion strength of stud type electrode | 100 to 400 g per each electrode | 180 g per each electrode | 180 g per each electrode | 170 g per each electrode |

As is apparent from the evaluation results described in Table 4 to Table 9 described above, the biomedical electrode of this example was not dried even when stored under a low-humidity condition of 20° C.-20% RH outside a sealed pouch and sufficiently met the AAMI characteristics. However, when the biomedical electrode was stored under a low-humidity condition of 20° C.-20% RH outside a sealed pouch for 30 days, the AC impedance exceeded 1000 Ω and the adhesion strength was slightly increased. As a counter measure, when the biomedical electrode was stored in a sealed pouch with a zip lock fastener for resealing the opened sealed pouch, the AAMI characteristics and adhesion strength can be maintained at almost the same level for 30 days even when the biomedical electrode is stored under the low-humidity condition of 20° C.-20% RH outside the sealed pouch.

The conductive adhesive as a constituent material of the biomedical electrode is derived from the coating syrup solution N1-a or N1-b. It has been found that the adhesion level of the resulting biomedical electrode can be controlled by utilizing a difference between these two kinds of syrup solutions. That is, the difference between both syrup solutions lies in amount of a crosslinking agent to be added as is apparent from a comparison between Table 2 and Table 3. In case where a large amount of the crosslinking agent is added, the adhesive becomes rigid and, therefore, the adhesion level can be reduced.

Comparative Example

In this example, for the comparison purpose, an adhesive consisting of a microemulsion containing a hydrophobic adhesive phase and a hydrophilic conductive phase was prepared. The composition of the adhesive was similar to that of Example 1.

A mixture obtained upon mixing of the starting materials except for the above-described humectant was a transparent liquid. This means that a size of the hydrophobic phase and the hydrophilic phase is smaller than the wavelength of visible light. That is, this is because a domain phase of the emulsion has an average diameter of less than 0.02 μm.

On the other hand, when the humectant used in Example 1 was added to the above-prepared transparent liquid, the hydrophilic phase and the hydrophobic phase were separated as upper and lower layers in the container. This means that in the microemulsion containing a domain phase of the above-described size, use of an amino acid humectant is difficult to maintain a stable phase structure as in Example 1.

Example 2

To obtain the better resistance to drying (drying prevention effect) as described above, a large amount of the humectant is preferably added as possible. In this example, the procedure described in Example 1 was repeated, except that the coating syrup solution N1-a was prepared after the amount of the humectant (the same as that used in Example 1) in the precursor syrup solution N1 of Example 1 was changed, as shown in Table 10-1 to Table 10-7, so as to examine an influence of an increase in amount of the humectant on an improvement in resistance to drying. The precursor syrup solution prepared in this example is referred to as a "syrup number N2" for distinction from that of Example 1.

TABLE 10-1

(N2-0)

| | Raw materials | | Parts by weight | % by weight |
|---|---|---|---|---|
| Monomers | UV initiator | Irg. 184 | 0.05 | 0.053 |
| | AA | AA | 14 | 14.862 |
| | IOA | IOA | 14 | 14.862 |
| | Surfactant | SE-10N | 17.4 | 18.471 |
| | Aqueous monomer | MPEG550MA | 8 | 8.493 |
| | Plasticizer | PEG300 | 3 | 3.185 |
| Salt solution | Humectant | Aquadew | 0 | 0.000 |
| | 4% KCl | 4% KCl | 37.25 | 39.544 |
| | UV initiator | Irg. 2959 | 0.5 | 0.531 |
| | Total | | 94.2 | 100.000 |

TABLE 10-2

(N2-5)

| | Raw Materials | | Parts by weight | % by weight |
|---|---|---|---|---|
| Monomers | UV initiator | Irg. 184 | 0.05 | 0.050 |
| | AA | AA | 14 | 14.113 |
| | IOA | IOA | 14 | 14.113 |
| | Surfactant | SE-10N | 17.4 | 17.540 |
| | Aqueous monomer | MPEG550MA | 8 | 8.065 |
| | Plasticizer | PEG300 | 3 | 3.024 |
| Salt solution | Humectant | Aquadew | 5 | 5.040 |
| | 4% KCl | 4% KCl | 37.25 | 37.550 |
| | UV initiator | Irg. 2959 | 0.5 | 0.504 |
| | Total | | 99.2 | 100.000 |

TABLE 10-3

(N2-10)

| | Raw materials | | Parts by weight | % by weight |
|---|---|---|---|---|
| Monomers | UV initiator | Irg. 184 | 0.05 | 0.048 |
| | AA | AA | 14 | 13.436 |
| | IOA | IOA | 14 | 13.436 |
| | Surfactant | SE-10N | 17.4 | 16.699 |
| | Aqueous monomer | MPEG550MA | 8 | 7.678 |
| | Plasticizer | PEG300 | 3 | 2.879 |
| Salt solution | Humectant | Aquadew | 10 | 9.597 |
| | 4% KCl | 4% KCl | 37.25 | 35.749 |
| | UV initiator | Irg. 2959 | 0.5 | 0.480 |
| | Total | | 104.2 | 100.000 |

TABLE 10-4

(N2-15)

| | Raw materials | | Parts by weight | % by weight |
|---|---|---|---|---|
| Monomers | UV initiator | Irg. 184 | 0.05 | 0.046 |
| | AA | AA | 14 | 12.821 |
| | IOA | IOA | 14 | 12.821 |
| | Surfactant | SE-10N | 17.4 | 15.934 |
| | Aqueous monomer | MPEG550MA | 8 | 7.326 |
| | Plasticizer | PEG300 | 3 | 2.747 |
| Salt solution | Humectant | Aquadew | 15 | 13.736 |
| | 4% KCl | 4% KCl | 37.25 | 34.112 |
| | UV initiator | Irg. 2959 | 0.5 | 0.458 |
| | Total | | 109.2 | 100.000 |

TABLE 10-5

(N2-18)

| | Raw materials | | Parts by weight | % by weight |
|---|---|---|---|---|
| Monomers | UV initiator | Irg. 184 | 0.05 | 0.045 |
| | AA | AA | 14 | 12.478 |
| | IOA | IOA | 14 | 12.478 |
| | Surfactant | SE-10N | 17.4 | 15.508 |
| | Aqueous monomer | MPEG550MA | 8 | 7.130 |
| | Plasticizer | PEG300 | 3 | 2.674 |
| Salt solution | Humectant | Aquadew | 18 | 16.043 |
| | 4% KCl | 4% KCl | 37.25 | 33.200 |
| | UV initiator | Irg. 2959 | 0.5 | 0.446 |
| | Total | | 112.2 | 100.000 |

TABLE 10-6

(N2-22)

| | Raw materials | | Parts by weight | % by weight |
|---|---|---|---|---|
| Monomers | UV initiator | Irg. 184 | 0.05 | 0.043 |
| | AA | AA | 14 | 12.048 |
| | IOA | IOA | 14 | 12.048 |
| | Surfactant | SE-10N | 17.4 | 14.974 |
| | Aqueous monomer | MPEG550MA | 8 | 6.885 |
| | Plasticizer | PEG300 | 3 | 2.582 |
| Salt solution | Humectant | Aquadew | 22 | 18.933 |
| | 4% KCl | 4% KCl | 37.25 | 32.057 |
| | UV initiator | Irg. 2959 | 0.5 | 0.430 |
| | Total | | 116.2 | 100.000 |

TABLE 10-7

(N2-40)

| | Raw materials | | Parts by weight | % by weight |
|---|---|---|---|---|
| Monomers | UV initiator | Irg. 184 | 0.05 | 0.036 |
| | AA | AA | 14 | 10.057 |
| | IOA | IOA | 14 | 10.057 |
| | Surfactant | SE-10N | 17.4 | 12.500 |
| | Aqueous monomer | MPEG550MA | 8 | 5.747 |
| | Plasticizer | PEG300 | 3 | 2.155 |
| Salt solution | Humectant | Aquadew | 0 | 0.000 |
| | 4% KCl | 4% KCl | 45 | 32.328 |
| | UV initiator | Irg. 2959 | 37.25 | 26.760 |
| | UV (Oil) | Irg. 2959 | 0.5 | 0.359 |
| | Total | | 139.2 | 100.000 |

In the above-described various precursor syrup solutions, since the humectant is not added to the precursor syrup solution N2-0 for reference described in Table 10-1, this syrup solution was a transparent and stable micro-emulsion. In precursor syrup solutions N2-5, N2-10, N2-15, N2-18, N2-22 and N2-40 shown in the following other amount of the humectant is changed as described in the tables.

The procedure described in Example 1 was repeated. As a result, each of the precursor syrup solutions N2-5, N2-10 and N2-15 wherein the amount of the humectant is 15% by weight (13.7% by weight) or less was a stable emulsion before conversion into a syrup (polymerization of hydrophobic monomer), while a mixed solution of precursor syrup N2-18, N2-22 and N249 wherein the humectant was added in the amount of 18 parts by weight (16.0% by weight) or more was separated into two phases. That is, it has been found that in the absence of the syrup formation process, it difficult to prepare a stable emulsion adhesive wherein a comparatively large amount of the humectant of amino acids was added.

To obtain the resistance to drying in a sufficiently high level with respect to the resistance to drying, the addition of 20% by weight of an amino acid humectant is desired. According to the present invention, a stable mini-emulsion containing a comparatively large amount of amino acids can be prepared by employing the above-described method for conversion into syrup.

The average domain diameter of the hydrophobic phase measured by a laser scattered particles analyzer of the precursor syrup solution N2-22 prepared by the method for conversion into syrup in accordance with the present invention was from 0.1 to 0.8 $\mu$m. Accordingly, both of the precursor syrup and conductive adhesive prepared by subjecting the precursor syrup solution to a polymerization treatment were opaque. The conductive wherein the humectant of this example was added had good electrical characteristics and resistance to drying in the level suited for use in the biomedical electrode.

Example 3

To obtain the better resistance to drying in a particularly suitable level as described above, about 20% by weight or more of the humectant is preferably added. In the precursor syrup solution for formation of an adhesive with these features, the size of the domain can be controlled by the composition and formulation. In light of the stability of the emulsion structure, the larger the amount of the electrolyte, the better. In this example, the procedure described in Example 1 was repeated, except that the coating syrup solution N1-a was prepared after the amount of the aqueous KCl electrolyte solution in the precursor syrup solution N1 of Example 1 was changed, as shown in Table 11-1 to Table 11-3, so as to examine an influence of an increase in amount of the aqueous 4% KCl electrolyte solution on the stability of the emulsion structure. The precursor syrup solution prepared in this example is referred to as a "syrup number N3" for distinction from that of Example 1.

TABLE 11-1

(N3-1)

| | Raw materials | | Parts by weight | % by weight |
|---|---|---|---|---|
| Monomers | UV initiator | Irg. 184 | 0.05 | 0.044 |
| | AA | AA | 14 | 12.275 |
| | IOA | IOA | 14 | 12.275 |
| | Surfactant | SE-10N | 16 | 14.029 |
| | Aqueous monomer | MPEG550MA | 6 | 5.261 |
| | Plasticizer | PEG300 | 2 | 1.754 |
| Salt solution | Humectant | Aquadew | 22 | 19.290 |
| | 4% KCl | 4% KCl | 39.5 | 34.634 |
| | UV initiator | Irg. 2959 | 0.5 | 0.438 |
| | | Total | 114.05 | 100.000 |

TABLE 11-2

(N3-2)

| | Raw materials | | Parts by weight | % by weight |
|---|---|---|---|---|
| Monomers | UV initiator | Irg. 184 | 0.05 | 0.047 |
| | AA | AA | 14 | 13.139 |
| | IOA | IOA | 14 | 13.139 |
| | Surfactant | SE-10N | 16 | 15.016 |
| | Aqueous monomer | MPEG550MA | 6 | 5.631 |
| | Plasticizer | PEG300 | 2 | 1.877 |
| Salt solution | Humectant | Aquadew | 22 | 20.648 |
| | 4% KCl | 4% KCl | 32 | 30.033 |
| | UV initiator | Irg. 2959 | 0.5 | 0.469 |
| | | Total | 106.55 | 100.000 |

TABLE 11-3

(N3-3)

| | Raw materials | | Parts by weight | % by weight |
|---|---|---|---|---|
| | UV initiator | Irg. 184 | 0.05 | 0.050 |
| | AA | AA | 14 | 14.134 |
| | IOA | IOA | 14 | 14.134 |

TABLE 11-3-continued (N3-3)

| | Raw materials | | Parts by weight | % by weight |
|---|---|---|---|---|
| Monomers | Surfactant | SE-10N | 16 | 16.153 |
| | Aqueous monomer | MPEG550MA | 6 | 6.058 |
| | Plasticizer | PEG300 | 2 | 2.019 |
| Salt solution | Humectant | Aquadew | 22 | 22.211 |
| | 4% KCl | 4% KCl | 24.5 | 24.735 |
| | UV initiator | Irg. 2959 | 0.5 | 0.505 |
| | | Total | 99.05 | 100.000 |

In the case of the precursor syrup solution N3-1 described in Table 11-1, the average domain diameter measured in the syrup solution before adding the water-soluble UV initiator and Irgacure 2959 (supra) was about 0.4 $\mu$m. The emulsion structure of this syrup solution was stable for several days.

In the case of the precursor syrup solution N3-2 described in Table 11-2, the average domain diameter measured in the syrup solution before adding the water-soluble UV initiator was about 0.2 $\mu$m. The emulsion structure of this syrup solution was also stable for several days.

In the case of the precursor syrup solution N3-3 (comparatively small amount of electrolyte) described in Table 11-3, the average domain diameter measured in the syrup solution before adding the water-soluble UV initiator was about 15 $\mu$m. It was a comparatively unstable macro-emulsion.

As is apparent from the above results, it has been found that an emulsion syrup, which contains a large amount of an electrolyte as possible and is stable, is preferred to prepare a conductive adhesive having good conductivity.

In the same procedure as in Example 1 except for using each of the precursor syrup solutions N3-1 to N3-3 in place of the precursor syrup solution N1, a conductive adhesive sheet of this example was made. It has been found that this adhesive sheet has electrical characteristics and resistance to drying in high level suited for use in the biomedical electrode.

Example 4

The same procedure as in Example 1 was repeated. In this examples, however, amino acids are contained as the humectant and an influence of a change in composition exerted on the characteristics of the resulting conductive adhesive was examined by using a precursor syrup solution containing raw material components that are different from those used in the aforementioned examples.

Table 12 described below is a table showing the composition of the precursor syrup solution mixed with the non-reactive surfactant, which is commercially available from Sigma Co under the product name of Brij 97. This precursor syrup solution was a white macro-emulsion.

TABLE 12

| | Raw materials | | Parts by weight | % by weight |
|---|---|---|---|---|
| Monomer | UV initiator | Irg. 184 | 0.05 | 0.039 |

TABLE 12-continued

|  | Raw materials | Parts by weight | % by weight |
|---|---|---|---|
|  | AA | AA | 19.6 | 15.403 |
|  | IOA | IOA | 14 | 11.002 |
|  | Surfactant | Brij 97 | 24 | 18.861 |
|  | Aqueous monomer | MPEG550MA | 11.1 | 8.723 |
|  | Plasticizer | PEG300 | 0.0 | 0.000 |
| Salt solution | Humectant | Aquadew | 17 | 13.360 |
|  | 4% KCl | 4% KCl | 41 | 32.220 |
|  | UV initiator | Irg. 2959 | 0.5 | 0.393 |
|  |  | Total | 127.25 | 100.000 |

In the same procedure as in Example 1 except for using the precursor syrup solution of the above composition in place of the precursor syrup solution N1, a conductive adhesive sheet of this example was made. It has been found that this adhesive sheet has electrical characteristics and resistance to drying in high level suited for use in the biomedical electrode.

Table 13 described below is a table showing the composition of the precursor syrup solution mixed with aforementioned amino acid PCA-Na (aqueous 50% solution) as the humectant. This precursor syrup solution was a white macro-emulsion.

TABLE 13

|  | Raw materials | Parts by weight | % by weight |
|---|---|---|---|
| Monomers | UV initiator | Irg. 184 | 0.060 | 0.1 |
|  | AA | AA | 11.50 | 19.0 |
|  | IOA | IOA | 16.50 | 27.3 |
|  | Surfactant | SE-10N | 4.00 | 6.6 |
|  | Aqueous monomer | MPEG550MA | 4.00 | 6.6 |
|  | Humectant | PCA-Na | 10.20 | 16.9 |
| Salt solution | 4% KCl | 4% KCl | 13.60 | 22.5 |
|  | UV initiator | Irg. 2959 | 0.60 | 1.0 |
|  |  | Total | 60.46 | 100.0 |

In the same procedure as in Example 1 except for using the precursor syrup solution of the above composition in place of the precursor syrup solution N1, a conductive adhesive sheet of this example was made. It has been found that this adhesive sheet has electrical characteristics and resistance to drying in high level suited for use in the biomedical electrode.

Example 5

In the same procedure as in Example 1 except for using the precursor syrup solution having the composition described in Table 14 in place of the precursor syrup solution N1, a conductive adhesive (adhesive sheet) of this example was made. The precursor syrup solution having the composition described below was an opaque emulsion and the adhesive as a final product obtained after curing was also an opaque conductive adhesive.

TABLE 14

|  | Raw materials | Parts by weight | % by weight |
|---|---|---|---|
| Monomers | UV initiator | Irg. 184 | 0.05 | 0.044 |
|  | AA | AA | 14 | 12.313 |
|  | IOA | IOA | 14 | 12.313 |
|  | Surfactant | SE-10N | 17.4 | 15.303 |
|  | Aqueous monomer | MPEG550MA | 6.4 | 5.629 |
|  | Plasticizer | PEG300 | 2.5 | 2.199 |
| Salt solution | Humectant | Aquadew | 22 | 19.349 |
|  | 4% KCl | 4% KCl | 37.25 | 32.762 |
|  | Crosslinking agent | TEGDAM | 0.1 | 0.088 |
|  |  | Total | 113.7 | 100.000 |

The adhesive sheet of this example was incorporated into the disposable ECG and EKG electrodes for electrocardiography, which were previously described with reference to FIG. 1 and FIG. 2, to make a biomedical electrode. Since a conductor used in the production of this biomedical electrode is that disclosed in aforementioned International Publication No. WO9741568, please see the description of the related portion of said publication with respect to the details.

Subsequently, the aging characteristics after the resulting biomedical electrode was put in the sealed pouch and stored at 66° C. for 6 weeks was evaluated in the same procedure as in Example 1. As a result, it has been found that the AAMI characteristics are not deteriorated and the biomedical electrode has good aging stability. It has also been found that the biomedical electrode has good satisfactory AAMI stability even in case where it was stored under a low-humidity condition of 20° C.-20% RH outside a sealed pouch for 30 days.

Example 6

In this example, a conductive adhesive (adhesive sheet) of this example was made in the same procedure as in Example 1 except for using the precursor syrup solution having the composition described in Table 15 below in place of the precursor syrup solution N1.

TABLE 15

|  | Raw materials | Parts by weight | % by weight |
|---|---|---|---|
| Monomers | Oil-soluble photo-initiator | Irg. 184 | 0.05 | 0.036 |
|  | AA | AA | 14 | 10.142 |
|  | IOA | IOA | 14 | 10.142 |
|  | Surfactant | E-mal E-70C | 9 | 6.520 |
|  | Hydrophilic monomer | MPEG550MA | 8 | 5.795 |
|  | Plasticizer | PEG300 | 3 | 2.173 |
| Cross-linking agent | Cross-linking agent | TEGDMA | 0.1 | 0.072 |
| Salt solution | Humectant | Aquadew | 50 | 36.221 |
|  | 4% KCl | KCl | 1.39 | 1.007 |
|  | Distilled water | DI water | 38 | 27.528 |

TABLE 15-continued

| | Raw materials | Parts by weight | % by weight |
|---|---|---|---|
| Water-soluble photo-initiator | Irg. 2959 | 0.5 | 0.362 |
| | Total | 138.04 | 100.000 |

In this example, to obtain the better resistance to drying, about 36% by weight or more of the amino acid humectant was contained in the precursor syrup solution and the non-reactive surfactant capable of exhibiting a higher surface active force than that of the surfactant used in Example 1, aforementioned Enal E-70C™ (sodium polyoxyethylene alkyl(C10–C16) ether sulfate) was used in place of the above surfactant used in Example 1. By using this surfactant, a stable mini-emulsion syrup could be obtained when the amount of the surfactant is from 5 to 8% by weight.

The adhesive sheet of the present invention was incorporated into the stud type electrode described previously with reference to FIG. 3 to make a biomedical electrode.

In the same procedure as in Example 1, the characteristics of the resulting biomedical electrode was evaluated. As a result, the measurement results described in Table 16 and Table 17 below were obtained.

TABLE 16

Aging stability of a stud type biomedical electrode in a sealed pouch at 66° C.

| Tests | AAMI specification | Initial | 3 weeks | 6 weeks |
|---|---|---|---|---|
| DC offset potential | 100 mV or less | −0.1 mV | −0.3 mV | 0.0 mV |
| AC impedance | 2000 Ω or less | 270 Ω | 353 Ω | 237 Ω |
| Offset potential after 5 seconds have passed since defibrillation | 100 mV or less | 12.3 mV | 14.6 mV | 16.6 mV |
| Recovery speed after 5 seconds have passed since defibrillation | 0 to −1.0 mV/s | −0.3 mV/s | −0.4 mV/s | −0.4 mV/s |
| Adhesion strength of stud type electrode | 100 to 400 g per each electrode | 150 g per each electrode | 210 g per each electrode | 200 g per each electrode |

TABLE 17

Resistance to drying of a stud type biomedical electrode under 20° C.-20% RH outside a sealed pouch

| Tests | AAMI specification | Initial | 20 days | 30 days |
|---|---|---|---|---|
| DC offset potential | 100 mV or less | −0.1 mV | −0.7 mV | 2.5 mV |
| AC impedance | 2000 Ω or less | 270 Ω | 442 Ω | 675 Ω |
| Offset potential after 5 seconds have passed since defibrillation | 100 mV or less | 12.3 mV | 14.8 mV | 19.7 mV |
| Recovery speed after 5 seconds have passed since defibrillation | 0 to −1.0 mV/s | −0.3 mV/s | −0.4 mV/s | −0.4 mV/s |
| Adhesion strength of stud type electrode | 100 to 400 g per each electrode | 150 g per each electrode | 150 g per each electrode | 120 g per each electrode |

As is apparent from the evaluation results described in Table 16 and Table 17 described above, the biomedical electrode made from the conductive adhesive of this example was hardly dried and the AC impedance was inhibited to a low value such as 675 Ω even after drying under a low-humidity condition of 20° C.-20% RH for 30 days. Without using the sealed pouch with a zip lock fastener, sufficient AAMI characteristics and adhesion strength can be maintained outside the pouch. Furthermore, sufficient AAMI characteristics and adhesion strength can be maintained even after an aging test.

Effect of the Invention

As described above, according to the present invention, there can be provided a conductive adhesive, which can enhance the moisturizing effect to effectively prevent drying, because high-performance humectants such as amino acids can be contained in the conductive adhesive and, in that case, the structure can be maintained in the effective state (e.g. state capable of exhibiting sufficient adhesion). According to the present invention, a high-performance biomedical electrode can be provided by using such a conductive adhesive.

What is claimed is:

1. A conductive adhesive comprising:
    (A) a first phase comprising at least one hydrophilic polymer, an aqueous electrolyte solution and at least one amino acid humectant, and
    (B) a second phase comprising at least one hydrophobic adhesive polymer,
        wherein the first phase is a continuous phase and the second phase is a domain phase dispersed in the first phase, and wherein the domain phase has an average diameter within a range from about 0.02 μm to about 1 mm.

2. The conductive adhesive of claim 1 wherein the amino acid humectant has at least one member selected from the group consisting of trimethylbetaine, DL-pyrrolidonecarboxylic acid (PCA) and sodium DL-pyrrolidonecarboxylate.

3. The conductive adhesive of claim 1 wherein the content of the humectant is in the range of about 10 to about 40% by weight based on a total amount of the conductive adhesive.

4. The conductive adhesive of claim 1 wherein the content of the humectant is in the range of about 15 to about 37% by weight based on a total amount of the conductive adhesive.

5. A biomedical electrode comprising an adhesive layer containing a conductive adhesive which comprises:
    (A) a first phase comprising at least one hydrophilic polymer and at least one amino acid humectant; and
    (B) a second phase comprising at least one hydrophobic adhesive polymer;

wherein the first phase is a continuous phase and the second phase is a domain phase dispersed in the first phase, and the domain phase has an average diameter within a range from about 0.02 μm to about 1 mm, and an electrode terminal connected with the adhesive layer.

6. A method of forming a conductive adhesive comprising: (1) subjecting a stock solution containing (a) an aqueous medium containing a first monomer capable of forming a hydrophilic polymer by polymerization, an aqueous electrolyte solution and an amino acid humectant and (b) a second monomer capable of forming a hydrophobic adhesive polymer by polymerization, which is contained in the aqueous medium, to a partial polymerization treatment so as to form a precursor syrup solution; and (2) further subjecting the precursor syrup solution to a polymerization treatment.

* * * * *

UNITED STATES PATENT AND TRADEMARK OFFICE
CERTIFICATE OF CORRECTION

PATENT NO. : 6,623,664 B2
DATED : September 23, 2003
INVENTOR(S) : Takaki Shunsuke It is certified that error appears in the above-identified patent and that said Letters Patent is hereby corrected as shown below:

Column 2,
Line 43, replace "electode" with -- electrode --;

Column 8,
Line 18, replace "fmal" with -- final --;
Lines 54 and 62, insert the word -- the -- before the word "case";

Column 9,
Line 47, replace "pyrroldione" with -- pyrrolidone --;

Column 10,
Line 66, replace "thoxanthone" with -- thioxanthone --;

Column 11,
Lines 1 and 10, replace "4substituted" with -- 4-substituted --;
Line 12, replace "trirethylaminopropozy" with -- trimethylaminopropoxy --;
Line 13, replace "trimethylaminopropozy" with -- trimethylaminopropoxy --;

Column 12,
Line 36, replace "dimetyhylpentanenitrile" with -- dimethylpentanenitrile --;

Column 13,
Line 22, replace "codensate" with -- condensate --;
Line 27, replace "noninic" with -- nonionic --;
Line 49, replace "Adekareasor$^{TM}$" with -- Adekareasorp$^{TM}$ --;
Line 52, replace "Assahi Denka" with -- Asahi Denki --;
Line 56, replace "Emale$^{TM}$" with -- Emal$^{TM}$ --;
Line 51, replace "$\chi$" with -- $\omega$ --;

Column 15,
Line 5, replace "require" with -- required --;

Column 16,
Line 30, replace "finctions" with -- functions --;
Line 51, replace "Lydal" with -- Lydal --;

Column 17,
Line 49, insert the word -- the -- following the word "case";

UNITED STATES PATENT AND TRADEMARK OFFICE
CERTIFICATE OF CORRECTION

PATENT NO. : 6,623,664 B2
DATED : September 23, 2003
INVENTOR(S) : Takaki Shunsuke It is certified that error appears in the above-identified patent and that said Letters Patent is hereby corrected as shown below:

Column 18,
Line 42, replace "Satomer" with -- Sartomer --;
Line 49 and 51, replace "Adekareasoap$^{TM}$" with -- Adekareasorp$^{TM}$ --;
Line 50, replace "Asahi Denka" with -- Asahi Denki --;

Column 19,
Line 54, replace "TV" with -- UV --;

Column 20,
Line 49, insert the word -- the -- before the word "case";

Column 21,
Line 5, delete "have" following "have";

Column 22,
Line 45, replace "200" with -- 100 --;

Column 23,
Table 7, insert -- eletrode -- following "each";

Column 25,
Line 37, insert the word -- the -- following the word "case";

Column 28,
Line 36, insert -- tables, the -- following "other"
Line 44, replace "N249" with -- N2-49 --;
Line 47, insert -- is -- following "it";

Column 30,
Line 49, replace "examples," with -- example, --;

Column 32,
Line 14, replace "TEGDAM" with -- TEGDMA --;
Line 38, insert the word -- the -- following the word "case";
Line 58, replace "E-mal" with -- Emal --;

UNITED STATES PATENT AND TRADEMARK OFFICE
CERTIFICATE OF CORRECTION

PATENT NO.      : 6,623,664 B2
DATED           : September 23, 2003
INVENTOR(S)     : Takaki Shunsuke It is certified that error appears in the above-identified patent and that said Letters Patent is hereby corrected as shown below:

<u>Column 32,</u>
Line 18, replace "Enal" with -- Emal --

Signed and Sealed this

First Day of June, 2004

JON W. DUDAS
*Acting Director of the United States Patent and Trademark Office*